US007037508B2

(12) United States Patent
Thiel et al.

(10) Patent No.: US 7,037,508 B2
(45) Date of Patent: May 2, 2006

(54) PESTIVIRUS MUTANTS AND VACCINES CONTAINING THE SAME

(75) Inventors: Heinz-Jürgen Thiel, Giessen (DE); Paul P. Becher, Fronhausen (DE); Michaela M. Orlich, Giessen (DE)

(73) Assignee: Akzo Nobel NV (NL)

( * ) Notice: Subject to any disclaimer, the term of this patent is extended or adjusted under 35 U.S.C. 154(b) by 0 days.

(21) Appl. No.: 09/839,796

(22) Filed: Apr. 19, 2001

(65) Prior Publication Data

US 2002/0086033 A1 Jul. 4, 2002

(30) Foreign Application Priority Data

Apr. 21, 2000 (EP) .......................................... 00201421

(51) Int. Cl.

| | |
|---|---|
| *A61K 39/12* | (2006.01) |
| *A01N 63/00* | (2006.01) |
| *C12Q 1/70* | (2006.01) |
| *C12N 7/00* | (2006.01) |
| *C12N 7/01* | (2006.01) |
| *C12N 7/02* | (2006.01) |
| *C12N 7/04* | (2006.01) |
| *C12N 7/08* | (2006.01) |
| *C07H 21/04* | (2006.01) |

(52) U.S. Cl. ................................ 424/218.1; 424/204.1; 424/93.1; 435/5; 435/91.33; 435/235.1; 435/236; 435/237; 435/239; 536/23.72

(58) Field of Classification Search ............. 424/204.1, 424/199.1, 93.1, 205.1, 218.1, 225.1; 536/24.1, 536/241, 23.72; 435/5, 91.33, 235.1, 236, 435/237, 239

See application file for complete search history.

(56) References Cited

FOREIGN PATENT DOCUMENTS

| | | | |
|---|---|---|---|
| EP | 0 965 639 | A | 12/1999 |
| WO | WO 99 55366 | A | 11/1999 |

OTHER PUBLICATIONS

Frolov et al. RNA. 1998; 4: 418–435.*

Grooms et al. Journal of Veterinary Diagnostic Investigation. 1998; 10 (2): 130–134, abstract only.*

Becher et al. Journal of Virology. 1998; 72 (6): 5165–5173.*

Thiel et al. " Pestiviruses", Fields Virology, 3rd edition. 1996. Lippencott–Raven, Philadelphia: 1059–1073.*

Chon SK et al: "Genetic analysis of the internal ribosome entry segment of Bovine Viral Diarrhea Virus" Virology, vol. 251, No. 2, Nov. 1998, pp. 370–382.

Becher P et al: Mutations in the 5' nontranslated region of Bovine Viral Diarrhea Virus result in altered growth characteristics, Journal of Virology, vol. 74, No. 17, Sep. 2000, pp. 7884–7894.

* cited by examiner

*Primary Examiner*—James Housel
*Assistant Examiner*—Shanon Foley
(74) *Attorney, Agent, or Firm*—Mark W. Milstead; William M. Blackstone

(57) ABSTRACT

The present invention is directed to attenuated pestivirus mutants, which have a reduced ability to replicate as exhibited by a small plaque size. The mutations are in the 5' nontranslated region of the viral genome. These mutant viruses are useful as live vaccines in the control of bovine viral diarrhea, border disease and classical swine fever.

23 Claims, 8 Drawing Sheets

Figure 1

| | IF 24h p.t. | Infectivity (PFU/μgRNA) |
|---|---|---|
| CP7-5A |  | $

PESTIVIRUS MUTANTS AND VACCINES CONTAINING THE SAME

FIELD OF THE INVENTION

The present invention is directed to attenuated pestivirus mutants, which have a reduced ability to replicate, which is exhibited by a small plaque size. Such viruses are useful as live vaccines in the control of bovine viral diarrhea, classical swine fever and border disease of sheep. The invention is particularly directed to attenuated bovine viral diarrhea viruses that have been genetically engineered for reduced replication in the host, and which are useful in live vaccines for cattle.

BACKGROUND OF THE INVENTION

Pestiviruses cause economically important diseases in animals worldwide. The genus Pestivirus, within the family Flaviviridae, comprises three species: bovine viral diarrhea virus (BVDV), classical swine fever virus (CSFV), and border disease virus (BDV). The presence of a fourth separate group of pestiviruses comprising isolates from cattle and sheep has been recently described, and it is now generally accepted to refer to this additional species as BVDV-2; consequently, classical BVDV strains are named BVDV-1. See Becher et al., Virology 209(1):200–206 (1995).

BVDV-1 and BVDV-2 both cause acute infections in cattle (diarrhea, fever, hemorrhagic syndrome) as well as (if the infection occurs during pregnancy) abortion, malformation of the fetus and persistent infection of the calves. Persistently infected animals represent the major reservoir of the virus, and such animals may come down with the fatal mucosal disease (MD).

Classical swine fever virus (CSFV), formerly called hog cholera virus, is responsible for classical swine fever (CSF) or hog cholera (HC). Border disease virus (BDV) is typically found in sheep and causes border disease (BD). Symptoms similar to MD in cattle have also been shown to occur after intrauterine infection of lambs with BDV. For a review of pestiviruses, see Thiel et al., The pestiviruses., In Fields Virology, Fields et al. (eds.) (Lippincott-Raven, Philadelphia), pp.1059–1073 (1996).

Vaccines based on live or killed viruses, as well as of recombinant expression systems expressing viral proteins, have been developed for BVDV and CSFV and are presently used. The presently used live vaccines contain a more or less attenuated strain that replicates in the host. Attenuation may have been achieved by multiple passaging in homologous or heterologous cell culture (at suboptimal temperatures). However, these strains may still lead to transplacental infection and thereby cause fetal death, growth malformation, and persistent infection in the offspring.

A live vaccine strain with defined mutations resulting in a strong attenuation would avoid the disadvantages of the present generation of vaccines. Full-length infectious DNA copies have recently been constructed for BVDV (Meyers et al., J. of Virology 70:8606–8613 (1996)) and CSFV (Meyers et al., J. of Virology 70:1588–1595 (1996)). Their availability enables scientists to perform reverse genetic engineering in order to develop attenuated strains of BVDV or CSFV. However, it is still not known which region(s) of the genome should and can be modified to lead to a safe and effective vaccine strain.

Because of the importance of a safe and effective prophylaxis and treatment of pestivirus infections, there is a strong need for live and specifically attenuated vaccines with a high potential for induction of immunity as well as a defined basis of attenuation resulting in a significant reduction in the ability to replicate in the host.

BRIEF SUMMARY OF THE INVENTION

Therefore, the technical problem underlying the present invention is to provide safe, specifically attenuated pestiviruses for use as live attenuated vaccines with an ability to induce protective immunity.

The solution to the above technical problem is achieved by the present invention, which provides an attenuated pestivirus which contains a mutation in the 5' nontranslated region (NTR) of the pestivirus genome.

DETAILED DESCRIPTION OF THE INVENTION

More specifically, the present invention is directed to a pestivirus which contains one or more mutations in the region containing stem-loops la and lb of the 5' nontranslated region (NTR) of the pestivirus genome, which mutation results in a small plaque size phenotype, in which the expression of the viral polyprotein is under the control of a homologous internal ribosome entry site (IRES) and the sequence GUAU is at the 5' end of the pestivirus genome.

Complementary bases of single-stranded RNA can pair to form stem-loop structures, also referred to as hairpins. Two such stem-loop structures, termed la and lb (or B1' and B1, respectively, by some authors), appear at the 5' non-translated region of pestiviruses, and precede the IRES element. See FIG. 1B, which shows the secondary structure of the 5' NTR of BVDV). For BVDV, the stem-loops la and lb comprise roughly nucleotides 1–73 of the BVDV genome. By the present invention, it has been discovered that the region containing these stem-loop structures is not essential for viral replication.

The IRES element is where translation initiation of the pestivirus polyprotein occurs, and is located within the 5'NTR and the 5' terminal region of the open reading frame (ORF). The 5' border of the pestivirus IRES is near nucleotide 75; the 5' terminal stem-loops la and lb are not required for IRES activity. See Chon et al., Virology 251:370–382 (1998). There is a general agreement that the 3' end of the IRES extends to the AUG initiation codon of the polyprotein.

Although the examples herein are directed to BVDV, the present invention is contemplated as applicable to all of the pestiviruses. This is particularly because BVDV, CSFV and BDV are structurally and serologically related to one another. The overall genetic relatedness among the pestiviruses is well defined by the extent of sequence homology between the genomes of the viruses of this genus, which is 60–70%. More significantly, the primary and secondary structures of the 5'NTR of pestiviruses are similar. That is, the stem-loop structures in this region are the same. See Deng et al., Nucleic Acids Res., 21:1949–1957 (1993); Becher et al., J. Virol. 72:5165–5173 (1998); and Pestova et al., Genes & Development 12:67–83 (1998).

By the term "mutation" is meant that there is a change in the nucleic acid sequence as compared to the parent, wild-type virus, and may be a substitution, insertion and/or deletion of nucleotides. The mutation(s) is such that the virus exhibits a small plaque size phenotype in comparison to a typical wild-type strain. The mutation is made in the 5'NTR of the pestivirus genome, in the region containing stem-loops 1a and 1b. Thus, the IRES is not affected and the viral polypeptide can still be translated. Therefore, the mutated virus may produce the full complement of pestiviruses proteins, allowing for maximum immunogenicity of the attenuated virus when used as a vaccine. On the other hand, mutations in addition to those in the 5' NTR stem-loop 1a and 1b region occurring in the polyprotein region of the pestivirus genome, which result in non-functionality or non-expression of a viral protein, are also contemplated by the present invention. Such pestivirus mutants could function as marker vaccines.

By "small plaque size" phenotype is meant that the pestiviruses exhibit plaques that are on average at least about 50% smaller than the parent, wild-type virus under identical conditions. Such a reduced plaque size is indicative of a growth-restricted phenotype, and thus a significant decrease in virulence. Plaque size can be determined by the following method. A host cell line (in particular, MDBK for BVDV) is transfected with 2 μg of RNA which has been synthesized in vitro from full-length cDNA infectious clones, and 10-fold serial dilutions of transfected cells together with $2 \times 10^6$ untreated cells are seeded into six-well dishes. After incubation at 37° C. for 4 hours, the attached cells are overlaid with semisolid medium containing 0.6% low-melting-point agarose and 5% horse serum. After 6 days of incubation at 37° C., the agarose overlays are removed, and the plaques can be visualized by, for instance, an immunostain. Plaque sizes are measured and an average plaque size can then be determined.

Typically, the average plaque size of pestiviruses is about 3–4 millimeters, by the above assay. Thus, for the present invention, in order to be considered as having a small plaque size phenotype, the average plaque size for the mutant should be between 0.2 and 2.0 mm, preferably between 0.5 and 1.5 mm, more preferably between 0.7 and 1.2 mm, and most preferably about 0.8 mm in plaque size based upon the above described plaque assay.

The mutants of the present invention should have a homologous IRES. This means that the mutants should have a pestivirus IRES, whether its own or that of another pestivirus. Thus, a mutant BVDV could have a BVDV IRES element or a CSFV or BDV IRES element. Preferably, however, the pestivirus mutant of the present invention contains its own IRES element (i.e., BVDV mutants have a BVDV IRES, CSFV mutants have a CSFV IRES, etc.)

It is required that the 5' end of the genome of the pestivirus mutant have the sequence 5'-GUAU. This sequence was found by the present inventors to be necessary for replication; without this sequence replication is severely reduced, and therefore not amenable to vaccine production. It was also found by the present inventors, however, that if the entire region preceding the IRES (i.e., stem-loops 1a and 1b) was deleted, replication was severely reduced even with the presence of the 5'-GUAU sequence. (This is in contrast to Frolov et al., RNA, 4:1418–1435 (1998), which showed that BVDV-HCV chimeras that contained the GUAU sequence but did not contain BVDV stem-loops 1a and 1b, were not dramatically altered in replication ability.) Such mutants are, therefore, not contemplated in the present invention.

Preferably, the pestivirus of the present invention has one or more mutations in stem-loop 1a or in stem-loops 1a and 1b of the 5'NTR. These stem-loop structures are in the region 5' to the IRES, and are shown in FIG. 1B. It was found by the present inventors that if the conserved sequence motif 5'-GUAU was retained at the 5' end of the genomic RNA, 5'NTR sequences with substitutions or deletions of various parts of stem-loop 1a or deletion of the entire 1a with part of 1b supported replication, but to a lower degree than the parent virus. On the other hand, if the entire loop region of 1b is deleted, there is almost a complete loss of replication.

Preferably, more than one mutation is made in the 5'NTR of the pestivirus. It is known that viruses with more than one mutation, in the case of a substitution or insertion, for instance, are more genetically stable than those with just one mutation.

More preferably, the pestivirus of the present invention has a deletion of one or more nucleotides. In particular, one can delete nucleotides 5–28 (with the numbering used in this specification being based on the genomic sequence of BVDV-1, strain CP7-5A, which is the same as the sequence shown in FIG. 1A as CP7-9A but with 4 fewer A residues after nucleotide 44) of stem-loop 1a and obtain mutants with the desired reduction in replication. Even more preferable are mutants with larger deletions, such as Δ2–31 (in other words a deletion of stem-loop 1a, but still having GUAU at the 5') and Δ5–57 (in other words, a deletion of stem-loop 1a and part of stem-loop 1b, but retention of the GUAU found in nucleotides 1–4 of stem-loop 1a). Other preferred mutants are those that have nucleotides 5–73 deleted (i.e., have stem-loops 1a and 1b deleted, leaving only the GUAU sequence 5' to the IRES), but that have either the sequence AU or CCU inserted between the GUAU and the 5' end of the IRES. That is, the 5' terminal sequence in these mutants is either GUAUAU or GUAUCCU. See FIG. 6D, clones M1 and M2. Most preferred of the deletion mutants is Δ2–31.

Preferably, when the loop portion of stem-loop 1b (i.e., the region downstream of nucleotide 44 for BVDV-1, CP7 strain) is present in the mutant of the present invention, there are only five adenosine (A) residues present in it. The inventors surprisingly found that five A residues results in a genetically stable BVDV in this loop region. Of course, genetic stability is important for live vaccines.

Preferably, the pestivirus of the present invention is BVDV-1 or BVDV-2.

The pestiviruses according to the present invention can be prepared using so-called "reverse genetic" techniques. Genetically manipulating the RNA of pestiviruses in vitro is not currently possible. However, cDNA can be synthesized from the RNA of the virus and cloned into a plasmid by techniques known in the art. Such constructs are known as infectious clones, because the cDNA clones can transcribe RNA in vitro which generates infectious virus in cells. Using infectious clones, one can manipulate the DNA to engineer mutant viruses. This technique is called reverse genetics.

Infectious clones of BVDV and CSFV are known (see the two Meyers et al. references, cited supra), and it is expected that BDV infectious clones can be constructed based on the same techniques. The infectious clones can be transfected into a cell culture suitable for growth of the virus. For example, infectious clones of BVDV can be transfected into bovine kidney cells (such as MDBK cells); infectious clones of CSFV can be transfected into porcine kidney cells (for example, PK-15 or SK-6). BDV clones could be similarly transfected into ovine or bovine cells.

Using the infectious clones, one can substitute, insert or delete nucleotides in the 5'NTR in accordance with the present invention using standard techniques, such as techniques for site-directed mutagenesis. A reduced ability to replicate can be ascertained with the mutants by measuring specific infectivity (i.e., the number of plaque forming units (PFUs) per μg RNA) or the $TCID_{50}$ in an appropriate cell culture. The small plaque phenotype can be determined by the plaque assay described above in this specification.

The present invention also encompasses vaccines comprising the pestivirus mutants. The term "vaccine" as used herein refers to a pharmaceutical composition comprising at least one immunologically active component that induces an immunological response in an animal and possibly, but not necessarily, additional components that enhance the immunological activity of the active component. The vaccine also comprises additional components typical to pharmaceutical compositions.

The pestivirus mutants of the present invention can be formulated into vaccines that comprise an effective dosage of live attenuated pestivirus, i.e. an amount of pestivirus that will induce immunity in the vaccinated animals against challenge by the virulent pestivirus, and comprises a pharmaceutically acceptable carrier or diluent, for example, physiological saline solution. Immunity is defined herein as the induction to a significant degree of a higher level of protection in a population of animals after vaccination as compared to an unvaccinated group. The precise dosage can be determined by the practitioner; a typical dose of live virus for a cattle vaccine, for instance, is between 5 and 7 $\log_{10}$ $TCID_{50}$ per dose.

To produce sufficient quantities of the virus mutants for vaccine purposes, the mutants can be grown in suitable cell culture and for example, in roller bottles or fermentators, with or without microcarriers.

Carriers in the vaccine composition may comprise stabilizers, preservatives and buffers. Suitable stabilizers are, for example, SPGA, carbohydrates (such as sorbitol, mannitol, starch, sucrose, dextran, glutamate or glucose), proteins (such as dried milk, serum albumin, casein, or proteins from other sources such as from plants or microorganisms), or degradation products thereof. Suitable buffers are, for example, alkali metal phosphates. Suitable preservatives are thimerosal, merthiolate and gentamicin. Diluents include water, aqueous buffer (such as buffered saline), alcohols and polyols (such as glycerol).

If desired, the live vaccine compositions according to the invention may contain an adjuvant. Non-limiting examples of suitable compounds and compositions with adjuvant activity include aluminum hydroxide, -phosphate, or -oxide, oil-in-water or water-in-oil emulsions based on, for example, a mineral oil, such as Bayol® or Marcol® or a vegetable oil such as vitamin E acetate, and saponins.

The vaccine according to the present invention may also contain one or more other immunogens of other microorganisms which are pathogenic to the animal being immunized. For instance, for cattle, additional immunogens can be derived from one or more of bovine rotavirus, bovine respiratory syncytial virus, bovine herpesvirus type 1, bovine coronaviruses, parainfluenza type 3 virus, bovine paramyxovirus, foot and mouth disease virus and *Pasteurella hemolytica*. For swine, such combination vaccines could include foot and mouth disease virus, pseudorabies virus, *Pasteurella multocida*, *Erysipelas rhusiopathiae*, and *Actinobacillus pleuropneumoniae*. For sheep, additional immunogens could be those from Toxoplasma and *Chlamydia psittaci*.

The vaccine may be in the form of a solution, suspension, or in a lyophilized or frozen form, and prepared using standard techniques. Both the preparation of the live pestivirus and the formulation of this with other immunogens, with or without adjuvant, are conventional, and include the mixing of the live attenuated pestivirus with a pharmaceutically acceptable carrier or diluent, optionally with other immunogens and optionally with an adjuvant. The preparation of vaccine compositions is inter alia described in "Handbuch der Schutzimpfungen in der Tiermedizin" (eds: Mayr, A. et al., Verlag Paul Parey, Berlin and Hamburg, Germany, 1984) and "Vaccines for Veterinary Applications" (eds: Peters, A. R. et al., Butterworth-Heinemann Ltd., 1993). For instance, as a non-limiting example, the vaccine could be prepared as follows: Cell culture supernatant containing the mutant pestivirus according to the invention is mixed with a stabilizer, and the mixture is subsequently lyophilized or dehydrated by other methods. Prior to vaccination, said mixture is then rehydrated in aqueous or non-aqueous solutions.

The present invention provides vaccines, or pharmaceutical compositions, which are particularly useful for the prophylaxis and treatment of pestivirus infections in animals. Therefore, a further aspect of the present invention relates to methods for the prophylaxis and treatment of pestivirus infections in animals characterized in that a vaccine according to the present invention is administered to an animal in need of such prophylaxis or treatment. The vaccines of the present invention can be administered by intramuscular or subcutaneous injection or via intranasal, intratracheal, oral, cutane, percutane or intracutane administration. Preferably, for BVDV vaccines, vaccination is intranasal or intramuscular, intramuscular being most preferred. Live vaccines for BVDV are preferably administered between about six months of age and the first insemination in dairy cattle.

The present invention is further characterized by reference to the following examples, it being understood that the invention is not limited thereto.

EXAMPLE 1

Generation of Infectious cDNA Clones of BVDV and Resulting CP7-5A Virus (A) Generation of Infectious cDNA Clone of BVDV After cDNA cloning of the genome of bovine viral diarrhea virus strain CP7, the full-length cDNA clone pA/BVDV was constructed (described in detail by Meyers et al., J. Virol. 70: 8606–8613). The 5' terminal sequence of the CP7 genomic RNA comprising the 5' proximal 21–23 nucleotides (nt) and the 3' terminal 33 nt (when compared to published sequences of other BVDV strains) were not determined; instead the respective terminal sequences of the heterologous BVDV-1 strain NADL were introduced into pA/BVDV.

(B) Generation of the Infectious cDNA Clone pCP7-5A

In order to establish an authentic infectious cDNA clone of BVDV CP7, the 5' and 3' terminal sequence of this virus were determined. After ligation of the viral genomic RNA, a nested RT-PCR assay (using sense primers located at the 3' end of the genome and antisense primers located in the 5' NTR of the genome) resulted in specific amplification of a cDNA fragment of the expected size which was subsequently cloned in a bacterial vector. Sequence analysis revealed that the unknown 5' terminal 21 nt differed at 9 positions from the sequences of BVDV-1 strains NADL and Osloss (FIG. 1A). Surprisingly, the ten clones analyzed for determination of the 5' and 3' terminal sequences of BVDV CP7 exhibited a marked variation with respect to the number of A residues following nucleotide position 44. While the previously reported CP7 full-length cDNA clone pA/BVDV comprised 8 A residues at this position, 9 to 26 A residues were present in the cDNA clones obtained in this study. With respect to the 3' terminal 33 nt of the CP7 genome, six nucleotide differences were found when compared to the 3' terminus of BVDV NADL, while only two nucleotides differed from the sequence of BVDV strain Osloss.

The BVDV CP7 full-length cDNA clones described here were constructed on the basis of pA/BVDV (see reference above) and the subgenomic cDNA clone HHDI9 (described in detail by Tautz et al., J. Virol. 73, 9422–9432) which contains a NheI-site and an SP6 RNA polymerase promoter immediately upstream of the viral cDNA. HHDI9 lacks the genomic region encoding the structural proteins as well as p7 and NS2; the 5' terminal 21 bases and the 3' terminal 33 bases of HHDI9 were derived from the BVDV Osloss sequence. An XhoI (nt 222–227 of the CP7-5A sequence)/ClaI (nt 11075–11080 of the CP7-5A sequence) fragment from pA/BVDV was inserted in plasmid HHDI9 predigested with XhoI and ClaI, resulting in the plasmid pCP7-Os. For construction of CP7 full-length cDNA clones carrying the authentic 5' terminus and 9, 20, and 26 A residues downstream of position 44, the respective cDNA clones obtained after RNA ligation/RT-PCR were used as templates for PCR with Ol 200R (corresponding to nt 235–252 of the CP7-5A sequence) and Ol CP7-SP6 ((SEQ ID NO:1) 5'-TACCCTAGCATTTAGGTGACACTATAGTATACGA GGTTAGGCAAGTTC-3'; the underlined region corresponds to nt 1–22 of the CP7-5A sequence; an SP6 RNA polymerase promoter preceded by a NheI-site is located directly upstream of the CP7-specific sequence). Finally, the NheI/XhoI fragment of pCP7-Os was replaced by the CP7-specific NheI/XhoI fragments carrying 9, 20, and 26 A residues following position 44, resulting in the full-length cDNA clones pCP7-9A, pCP7-20A, and pCP7-26A.

Infectious BVDV was recovered after transfection of full-length RNA transcribed in vitro from the cDNA constructs pCP7-9A, pCP7-20A, and pCP7-26A. For transcription of RNA, the full-length cDNA clones were digested to completion with SmaI, extracted with phenol-chloroform and precipitated with ethanol. One microgram of linearized plasmid DNA was transcribed with SP6 RNA Polymerase in 20 μl using standard conditions. For degradation of the template DNA, the reaction mixture was digested with 5 U of DNase I for 1 h at 37° C., followed by extraction with phenol-chloroform and precipitation with ethanol. Photometric quantification of the transcribed RNAs was carried out in a photometer. The quality and the calculated amount of each RNA were controlled by ethidium bromide staining of samples after agarose gel electrophoresis. RNA transcripts used for transfection contained >60% of full-length RNA. MDBK cells (obtained from the American Type Culture Collection, Rockville, Md., USA) were transfected by electroporation. For transfection, the confluent cells from a 10-cm-diameter dish were resuspended in 0.4 ml of PBS without $Ca^{2+}$ and $Mg^{2+}$, and mixed with 2 μg of in vitro transcribed RNA immediately before the pulse (950 μF and 180 V). The transfected cells were seeded on 2 six-well dishes and adjusted to 2 ml with medium containing 10% horse serum. After transfection of cells, the production of progeny virus was indicated by development of cytopathology. Infection of the transfected cells was confirmed by immunfluorescence analysis (IFA) using monoclonal antibodies against Erns, E2, and NS3/NS2–3 and by passaging of the recovered infectious virus.

To investigate the genetic stability of the 5' NTR mutants, the obtained viruses CP7-9A, CP7-20A, and CP7-26A were repeatedly passaged in MDBK cells and the lengths of 5' NTR fragments were determined after 10 passages by RT-PCR analysis using primers OI 200R and OI CP7-SP6 and subsequent sequence analysis of the cloned cDNA fragments. For each of the variants, the sequences of twelve independent clones were determined. Nucleotide sequence analysis showed multiple insertions (and deletions) of A residues downstream of position 44; for CP7-26A, up to 54 As were observed (FIG. 2). This demonstrates that each of the variants is genetically unstable.

For further characterisation of this phenomenon, a full-length cDNA clone carrying a stretch of 54 A residues (pCP7-54A) downstream of position 44 was constructed. Transfection of the RNA transcribed from pCP7-54A resulted in recovery of infectious virus which was passaged 10 times in MDBK cells and then subjected to nucleotide sequence analysis of the 5' NTR. Interestingly, deletions of A residues were detected for 11 of 12 investigated clones; for some clones only 5 A residues were found after position 44 (FIG. 2). As a next step, we constructed the full-length cDNA clone pCP7-5A which carries 5 A residues following position 44 using a cloning strategy identical to the one described above for construction of e.g. pCP7-9A. Transfection of RNA transcribed from pCP7-5A resulted in recovery of the infectious virus CP7-5A.

(1) Description of experiments demonstrating that a virus with 5 A residues following position 44 is genetically stable.

The genetic stability of CP7-5A was investigated after repeated passages in MDBK cells. After 10 passages, the lengths of 5' NTR fragments were determined by RT-PCR analysis using primers OI 200R and OI CP7-SP6 and subsequent sequence analysis of the cloned cDNA fragments. Sequence analysis revealed that all 12 investigated clones carried 5 A residues following position 44 (FIG. 2). This demonstrates that CP7-5A represents a genetically stable variant of BVDV CP7, while multiple insertions and deletions of A residues rapidly occurred in the 5' NTR of the other variants. Apart from the variable number of A residues, no other differences were observed in any of the analysed 5' NTR clones.

EXAMPLE 2

Materials and Methods for Generating the 5' NTR Mutant Viruses

The first set of mutations within the 5' terminal 30 nt of CP7-5A was designed to alter both the nucleotide sequence and predicted RNA secondary-structure of hairpin 1a at various positions. Hairpin 1a includes a stem which is formed by base-pairing of nt 1–10 of the CP7 genome to the complementary sequence of nt 21–30, while the remaining 10 nt (11–20) form an apical loop. The RNAs of mutants SL-1, SL-2, and SL-3 lack nucleotide(s) 2, 6–7, and 14–17, respectively. In addition, several mutants were constructed which contain nucleotide substitutions at positions 2–4 (SL-4), 5–7 (SL-5), 10–13 (SL-6), and 27–29 (SL-7). The RNAs of SL-8, SL-9, delta 2–31, delta 5–57, and delta 5–73 lack nucleotides 1–24, 2–29, 2–31, 5–57, and 5–73. The predicted RNA secondary structures of the (altered) hairpin 1a is shown in FIG. 5A. Construction of all CP7 full-length cDNA clones carrying mutations within the 5' NTR was based on the genetically stable cDNA clone pCP7-5A. Generation of the mutant cDNAs was performed in two consecutive steps. First, the respective mutation was introduced into the 5' terminal sequence of CP7 by PCR with sense primer OI-SL1, OI-SL2, OI-SL3, OI-SL4, OI-SL5, OI-SL6, OI-SL7, OI-SL8, OI-SL9, OI-delta 2–31, OI-delta 5–57, or OI-delta 5–73 (each encompassing the respective mutated sequence preceded by a NheI-site and the SP6 RNA polymerase promoter) and the antisense primer OI 200R using pCP7-5A as template. In a second step, NheI/XhoI fragments of the resulting clones were introduced into pCP7-5A predigested with NheI and XhoI. The sequences of the sense primers are as follows:

```
OI-SL1:    5'-TACGCTAGCATTTAGGTGACACTATAGATACGAGGTTAGGCAAGTTC-3'
           (SEQ ID NO:2)

OI-SL2:    5'-TACGCTAGCATTTAGGTGACACTATAGTATAAGGTTAGGCAAGTTC-3'
           (SEQ ID NO:3)

OI-SL3:    5'-TACGCTAGCATTTAGGTGACACTATAGTATACGAGGTTAAGTTCTCGTATACATATTGGAC-3'
           (SEQ ID NO:4)

OI-SL4:    5'-TACGCTAGCATTTAGGTGACACTATAGGCGACGAGGTTAGGCAAGTTCTCG-3'
           (SEQ ID NO:5)

OI-SL5:    5'-TACGCTAGCATTTAGGTGACACTATAGTATGTAAGGTTAGGCAAGTTCTCGTA-3'
           (SEQ ID NO:6)

OI-SL6:    5'-TACGCTAGCATTTAGGTGACACTATAGTATACGAGAACTGGCAAGTTCTCGTATACATAT-3'
           (SEQ ID NO:7)

OI-SL7:    5'-TACGCTAGCATTTAGGTGACACTATAGTATACGAGGTTAGGCAAGTTCTCGTCCCCATATTGGACACTCTAAAAATAATTAG-3'
           (SEQ ID NO:8)

OI-SL8:    5'-TACGCTAGCATTTAGGTGACACTATAGTATACATATTGGACACTCTA-3'
           (SEQ ID NO:9)

OI-SL9:    5'-TACGCTAGCATTTAGGTGACACTATAGACATATTGGACACTCTAA-3'
           (SEQ ID NO:10)

Delta 2-31: 5'-TACGCTAGCATTTAGGTGACACTATAGTATTGGACACTCTAAAAATAATTAG-3'
            (SEQ ID NO:11)

Delta 5-57: 5'-TACGCTAGCATTTAGGTGACACTATAGTATCCTAGGGGACAAAAATCCTC-3'
            (SEQ ID NO:12)

Delta 5-73: 5'-TACGCTAGCATTTAGGTGACACTATAGTATCCTCCTTAGCGAAGGC-3'
            (SEQ ID NO:13)
```

For all CP7 full-length cDNA clones carrying mutations within the 5' NTR, the sequence of the entire 5' NTR was verified by nucleotide sequencing. Transfection of full-length genomic RNA transcribed from the cDNA clones carrying the mutations resulted in recovery of infectious virus. Transcription of RNA and transfection of MDBK cells were carried out as described above.

EXAMPLE 3

Description of the Properties of the Mutants

For comparative analyses of the properties of the BVDV 5' NTR mutants, the transcription/transfection experiments using the whole set of mutants were performed in parallel and repeated several times. These analyses included determination of the specific infectivity of the respective genomic RNAs, IFA and determination of viral yields after transfection as well as determination of the average plaque size, growth rate and yield of the recovered mutant viruses.

After transfection of MDBK cells (as described above) with 2 μg of genomic RNA, one tenth of the transfected cells was used for a plaque assay in order to determine the specific infectivity of the RNA and the plaque sizes of the recovered viruses. 10-fold serial dilutions of transfected cells together with 2×10⁶ untreated MDBK cells were seeded into six-well dishes. After incubation at 37° C. for 4 h, the attached cells were overlaid with semisolid medium containing 0.6% low-melting-point agarose (Gibco-BRL) and 5% horse serum. The mutant viruses produced small plaques (0.5–1.4 mm) which were visualized by immunostaining. After 6 days of incubation at 37° C., the agarose overlays were removed, and the cells were washed with PBS and then fixed with acetone-methanol (1:1) for 1 h at −20° C. After incubation with a mixture of BVDV E2-specific monoclonal antibodies for 2 h, monolayers were washed twice with PBS-0.05% Tween 20, and then incubated with peroxidase-conjugated goat anti-mouse immunoglobulin (1/500 in PBS-0.05% Tween 20; Sigma-Aldrich Chemie GmbH, Steinheim, Germany). After 1 h, the monolayers were washed twice with PBS and plaques were visualized by using the peroxidase substrate 3-amino-9-ethyl-carbazole (Sigma-Aldrich Chemie GmbH).

The specific infectivity indicates the number of plaque forming units (PFU) per μg RNA. This parameter was determined after transfection of MDBK cells with a defined amount of in vitro transcribed genomic RNA by counting the number of independently produced viral plaques. For the RNA of CP7-5A, CP7-9A, CP7-20A, and CP7-26A, the infectivity was between $2.4 \times 10^5$ PFU/μg and $6.0 \times 10^5$ PFU/μg, while $8.0 \times 10^4$ PFU/μg and $8.0 \times 10^2$ PFU/μg were obtained for the RNAs transcribed from pCP7-54A and pCP7-T, respectively (FIG. 3 shows the results of a representative experiment). The specific infectivities of all other 5' NTR mutants with substitutions or deletions within the region comprising the predicted hairpins 1a and 1b were significantly reduced when compared to the parent construct CP7-5A. The specific infectivities of SL-2, SL-3, SL-5, SL-6, SL-7, SL-8, delta 2–31, and delta 5–57 are between $5.2 \times 10^3$ PFU/μg-$6.4 \times 10^4$ PFU/μg) and allow the recovery of reasonable amount of infectious progeny virus (see below). In contrast, for SL-1, SL-4, SL-9 and delta 5–73, the specific infectivity was near or below the level of detection. These differences correlated well with the amounts of cells expressing BVDV antigen as determined 24 h p.t. by immunofluorescence using Mabs against Erns, E2, and NS3 (see FIGS. 3, 5, and 6). The specific infectivities and the results of the IFA of all the mutants are shown in FIGS. 3, 5, and 6. Mutants which have at least 2-fold reduced infectivities (e.g. SL-2, SL-3, SL-5, SL-6, SL-7, SL-8, delta 2–31, and delta 5–57) are expected to be attenuated and thus would be useful as a live vaccines.

In addition, the virus titers obtained at different time points after transfection were determined for all the 5' NTR mutants (FIGS. 4, 5, and 6). After the indicated time intervals, aliquots (200 µl) of the cell culture supernatant were removed and used for titration on MDBK cells. The viral yields were determined as the titer of 50% tissue culture infectious dosis ($TCID_{50}$)/ml. When compared to CP7-5A, the virus titers obtained 1 day after transfection were reduced by a factor of at least 8 for all 5' NTR mutants. The respective differences correlated well with the specific infectivities and the portions of BVDV antigen-positive cells determined 24 h p.t.

Progeny virus recovered from the in vitro transcribed RNAs of CP7-5A, SL-2, SL-3, SL-5, SL-6, SL-7, SL-8, delta 2–31, and delta 5–57 was characterized by plaque assay on MDBK cells using dilutions of transfected cells. The transcript-derived parent virus CP7-5A formed plaques with an average size of 2.7 mm. Each of the mutants produced smaller plaques. SL-2, SL-5, and SL-7 produced plaques with an average size ranging from 1.2–1.4 mm, while plaques generated by SL-3, SL-6, SL-8, delta 2–31, and delta 5–57 had an average size ≦0.8 mm. The average plaque sizes of the individual mutants are shown in FIG. 7. The small plaque phenotype is a significant property of all 5' NTR mutants and demonstrates that the respective virus is retarded in growth and therefore can be used as a live vaccine virus. For practical purposes, such a mutant preferably grows to titers of at least $10^5$ $TCID_{50}$/ml. After passaging the mutant viruses in MDBK cells, we have demonstrated that e.g. delta 2–31 and delta 5–57 reach titres >$10^6$ $TCID_{50}$. The plaque phenotype of these passaged virus mutants are identical to the one observed immediately after transfection (see above).

For determination of growth kinetics, supernatants from cells transfected with the individual mutant RNAs were titrated and then used to infect $1 \times 10^6$ MDBK cells (in a six-well dish) at an MOI of 0.05. After adsorption for 1 h at room temperature, the cells were washed six times with PBS, and then overlaid with medium containing 10% horse serum followed by incubation over a 4-days period. After the indicated time intervals, aliquots (200 µl) of the cell culture supernatant were removed and used for titration on MDBK cells. The viral yields were determined as the titer of 50% tissue culture infectious dosis ($TCID_{50}$)/ml. The peak titer for CP7-5A and the 5' NTR mutants was achieved on day 3 postinfection. Mutants SL-2, SL-3, SL-5, SL-6, and SL-7 were about 10-fold reduced in their peak titers, while the peak titers reached by mutants delta 2–31 and delta 5–57 were about 100-fold lower compared to CP7-5A (FIG. 8A). Establishment of growth curves at 33° C. and 40.5° C. showed that neither CP7-5A nor any of the mutants exhibited a temperature-sensitive phenotype, at least with regard to these temperatures. These results demonstrate that the differences of growth kinetics correlate with the observed plaque sizes. Moreover, the growth restriction of the mutant viruses mirrors the reduction of specific infectivity detected for the individual RNAs (FIG. 7; see also FIGS. 5 and 6). Such growth restricted viruses can be used as live vaccine viruses.

For analysis of viral RNA synthesis, $1 \times 10^6$ MDBK cells were infected with transcript-derived virus at a MOI of 0.05 and processed in parallel to cells used for determination of the growth kinetics. Total cellular RNA was prepared 2 days postinfection, and used for Northern blot analysis. Five micrograms of glyoxylated RNA was separated in a phosphate-buffered 1.0% agarose gel containing 5.5% formaldehyde and transferred to Duralon-UV membranes (Stratagene, Heidelberg, Germany). Radioactive labelling of the probe, hybridization, and washing conditions were as described (J. Virol. 72: 8697–8704). A 2.5-kb NotI-NsiI fragment from the cDNA clone pA/BVDV was used as a probe. The viral genomic RNAs were visualized by autoradiography, and the intensity of bands was determined with a phosphorimager (FIG. 8B). CP7-5A RNA was more abundant than that of any of the mutant viruses. The RNA of SL-7 was next followed by lower amounts of RNA for SL-2, SL-3, SL-5, and SL-6. As expected based on its replication kinetics, the RNAs of delta 2–31 and delta 5–57 were least abundant. Northern blot analysis of RNAs prepared 3 days postinfection led to very similar results. It can be concluded that the amounts of viral RNAs detected correlated with the obtained virus titers.

To investigate the genetic stability, each mutant was repeatedly passaged in MDBK cells. Using RNAs from the 3rd tissue culture passage, the 5' and 3' terminal sequences were amplified by the above described RNA ligation/RT-PCR method and cloned in a bacterial vector; at least 10 independent clones were characterized for each mutant. Sequence analysis indicated the absence of any secondary mutations within the analyzed genomic regions of the mutants SL-2, SL-3, SL-5, SL-6, SL-7, SL-8, delta 2–31 and delta 5–57. In contrast, reversions or secondary mutations were found for SL-1, SL-4, SL-9, and delta 5–73. Genetic stability is considered to be an important criterion for a genetically engineered live virus vaccine.

After two tissue culture passages of the transfection supernatant of Δ5–73, higher titers of infectious virus (>$10^5$/ml) were obtained. Analysis of the 5' terminal sequences derived from 12 independent clones indicated the emergence of mutants with duplications of 2 nt (M1) or 3 nt (M2) near the 5' terminus of the genome (FIG. 6D). These results suggest that hairpins la and lb are not required for replication of pestiviruses, provided the sequence motif 5'-GUAU remains at the 5' terminus of the viral RNA.

Two additional mutants, termed R1 and R2, were generated after transfection of RNAs transcribed from CP7-5A -derived cDNA clones containing the 5' terminal sequence of mutant virus M1 or M2, which emerged after transfection with the delta 5–73 RNA. The mutant viruses R1 and R2 still contain the 5'-GUAU, but lack the hairpins la and lb.

The specific infectivities of the RNAs of R1 and R2 were significantly reduced when compared to the parent construct CP7-5A.

Further analyses were performed with R2. R2 exhibited a small plaque phenotype (average size <1.2 mm). The peak titer of R2 reached in bovine cells was >10-fold lower compared to CP7-5A. Furthermore, the amount of accumulated RNA was significantly reduced.

EXAMPLE 4

Further Studies on the Genetic Stability of Delta2–31, Delta5–75 and R2

To further study the genetic stability, the mutant viruses delta 2–31, delta 5–57, and R2 were passaged ten times in MDBK cells. Using RNAs from the 10th tissue culture passage, the 5' and 3' terminal sequences were amplified by the described RNA ligation/RT-PCR method and cloned in a bacterial vector. Sequence analysis of at least 4 clones for each of the three mutants indicated the absence of any secondary mutations within the analyzed part of the 5' NTRs. In addition, plaque assays performed with the mutant viruses delta 2–31, delta 5–57, and R2 obtained after 10

BRIEF DESCRIPTION OF THE DRAWINGS

Figure 1:
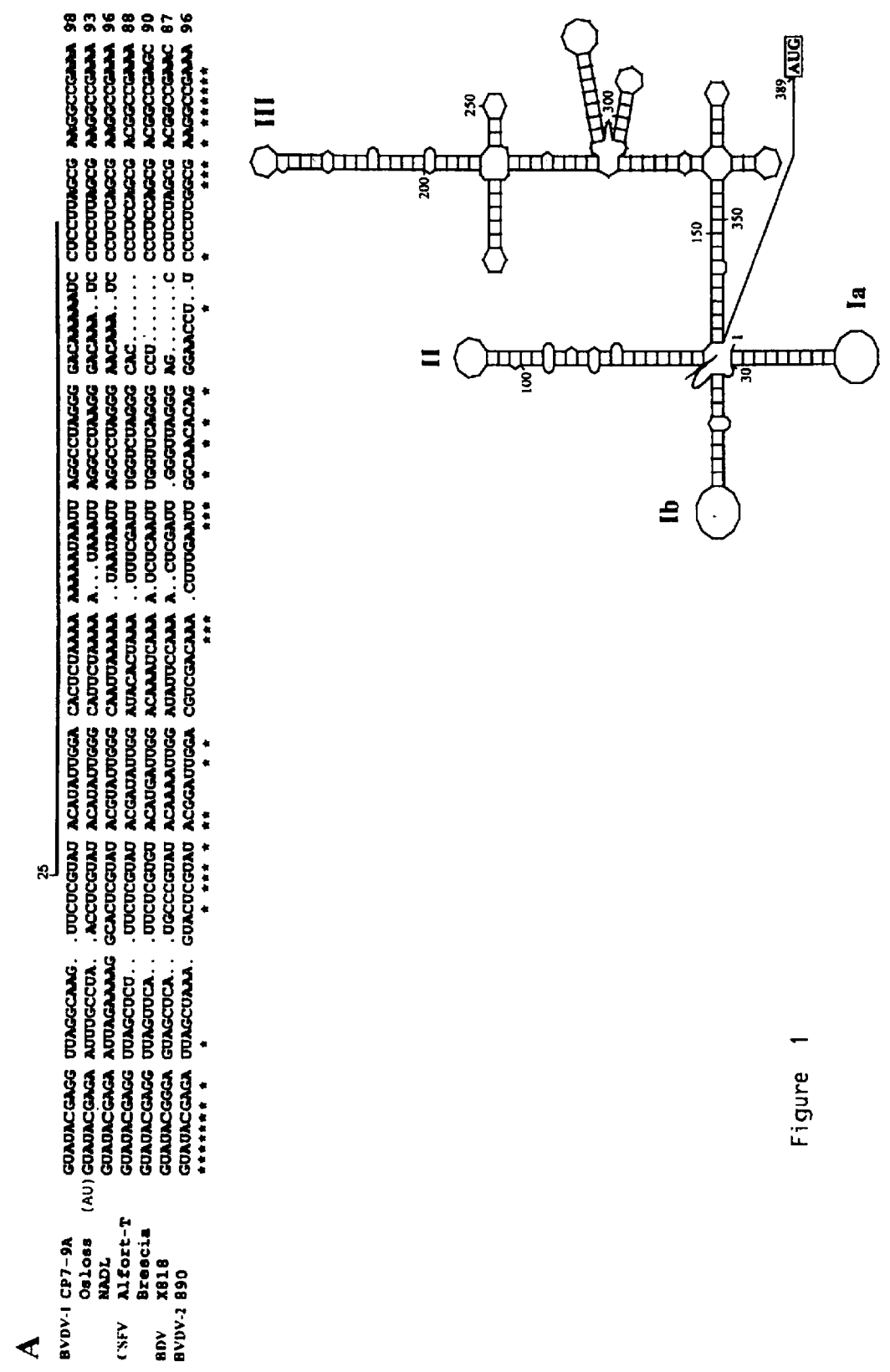

FIG. 1. 5' sequences of pestiviruses, in particular BVDV-1 strain CP7. (A) Alignment of the 5' terminal sequences of representative strains from the four pestivirus species. For BVDV-1 CP7, the consensus sequence was determined from 10 independent clones. Other sequences were extracted from the GenBank/EMBL database (BVDV-1 Osloss, BVDV-1 NADL, CSFV Alfort-T, CSFV Brescia, BDV X818, BVDV-2 890). Conserved nucleotides are indicated with an asterisk. (B) Predicted RNA secondary-structure of the 5' NTR of BVDV-1 CP7-9A. Modeling was performed with the computer programs RNAFOLD, MFOLD and FOLDANALYZE. In addition, the proposed structure is based on comparative sequence analysis. The initiation codon AUG is indicated.

SEQUENCE LISTING

<160> NUMBER OF SEQ ID NOS: 24

Figure 2:
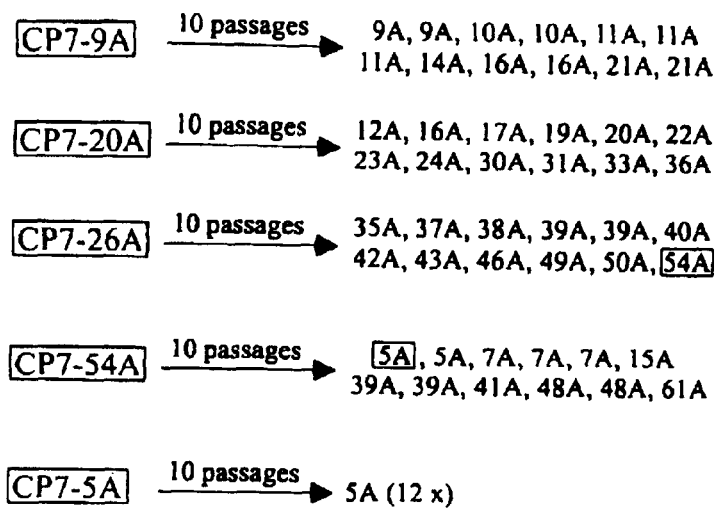
FIG. 2. Multiple insertions and deletions of A residues downstream of position 44 during propagation of BVDV 5' NTR mutants in bovine cells. After transfection with engineered full-length RNAs, the recovered BVDV mutants CP7-9A, CP7-20A, CP7-26A, CP7-54A, and CP7-5A were repeatedly passaged in MDBK cells. After 10 passages, the 5' NTR sequences and the numbers of A residues following position 44 were determined for each mutant by sequence analysis of 12 independent clones.
Figure 3:
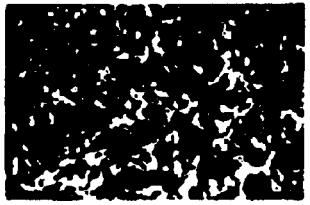
FIG. 3. Immunofluorescence (IF) analysis of MDBK cells at 24 h posttransfection (p.t) with engineered full-length RNAs of CP7-5A, CP7-9A, CP7-20A, CP7-26A, CP7-54A, and CP7-T (magnification, ×100). The specific infectivities of the BVDV CP7 mutant RNAs are indicated.
Figure 4:
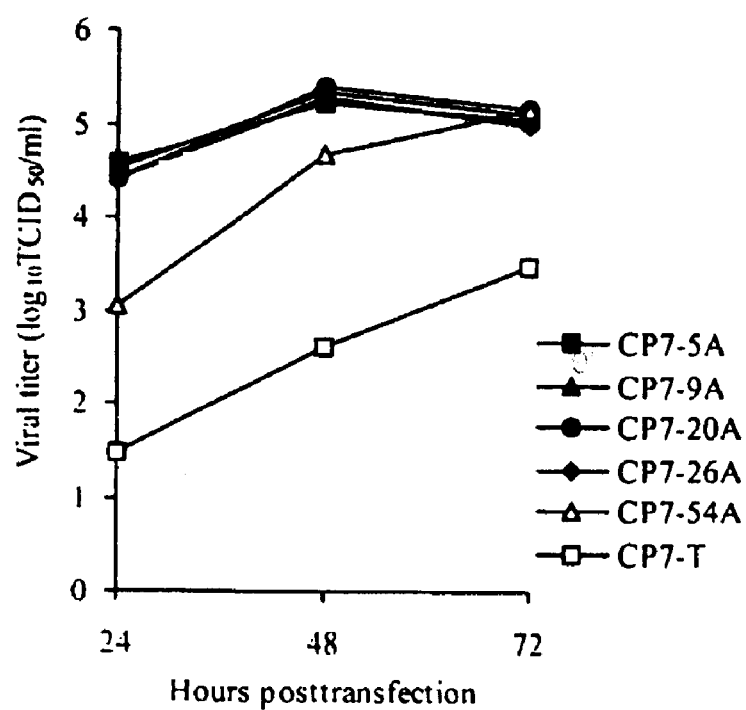
FIG. 4. Virus titers obtained for BVDV 5' NTR mutants CP7-5A, CP7-9A, CP7-20A, CP7-26A, CP7-54A, and CP7-T at 24, 48, and 72 h posttransfection. The titers of released virus were determined on MDBK cells.
Figure 5:
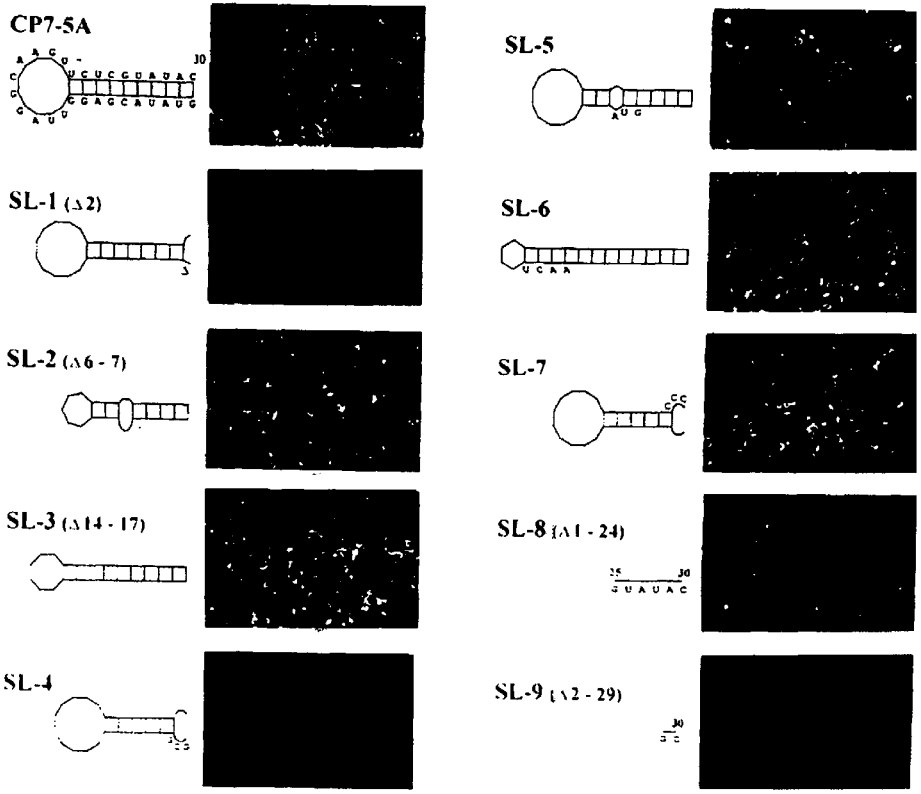
FIG. 5. Hairpin la mutants. (A) Computer-predicted RNA secondary-structures of BVDV hairpin la mutations and IF analysis of MDBK cells at 24 h posttransfection (p.t.) with full-length RNAs of CP7-5A, SL-1, SL-2, SL-3, SL-4, SL-5, SL-6, SL-7, SL-8, and SL-9 (magnification, ×100). Modeling was performed with the computer programs RNAFOLD and MFOLD. Deleted (Δ) and substituted nucleotides within hairpin la are indicated. (B) Specific infectivities of the BVDV mutant RNAs in MDBK cells and virus titers obtained at 24, 48, and 72 h p.t.
Figure 6:
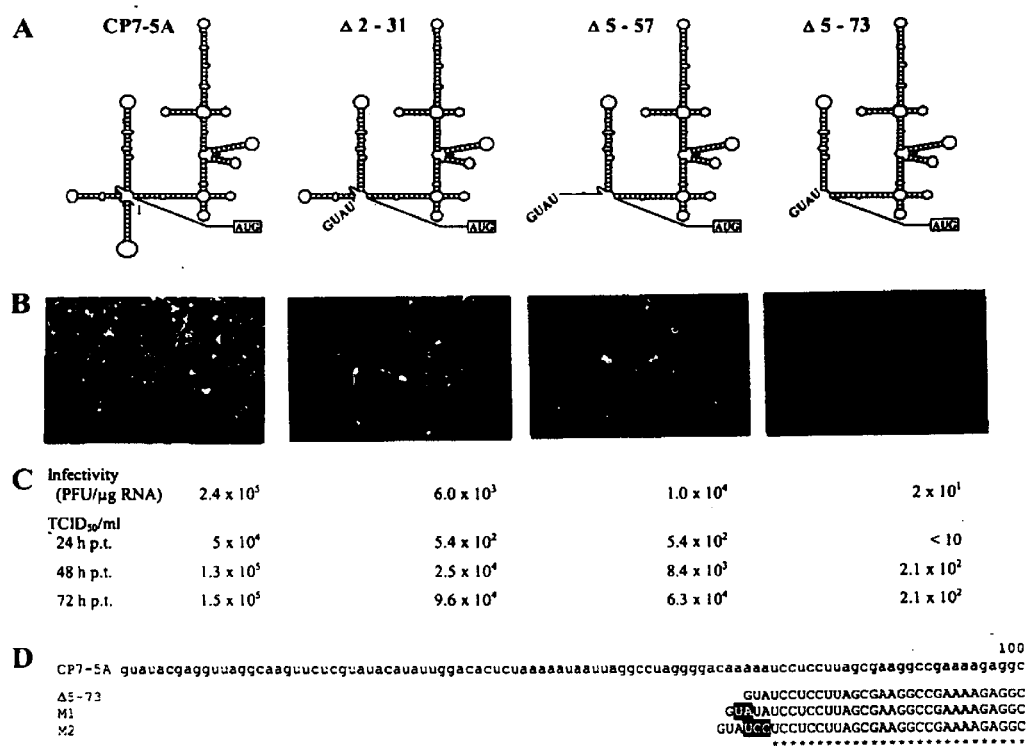
FIG. 6. Deletion of hairpins la and lb. (A) Schematic representation of the 5' NTR of BVDV CP7-5A and deletion mutants Δ2–31, Δ5–57, and Δ5–73. (B) IF analysis of MDBK cells at 24 h posttransfection (magnification, ×100). (C) Specific infectivities in MDBK cells and virus titers obtained at 24, 48, and 72 h p.t. (D) 5' terminal sequences of CP7-5A, Δ5–73, and mutant viruses M1 and M2 evolved after passaging of supernatants from cells transfected with Δ5–73 RNA. For M1 and M2, the inserted nucleotides are highlighted.
Figure 7:
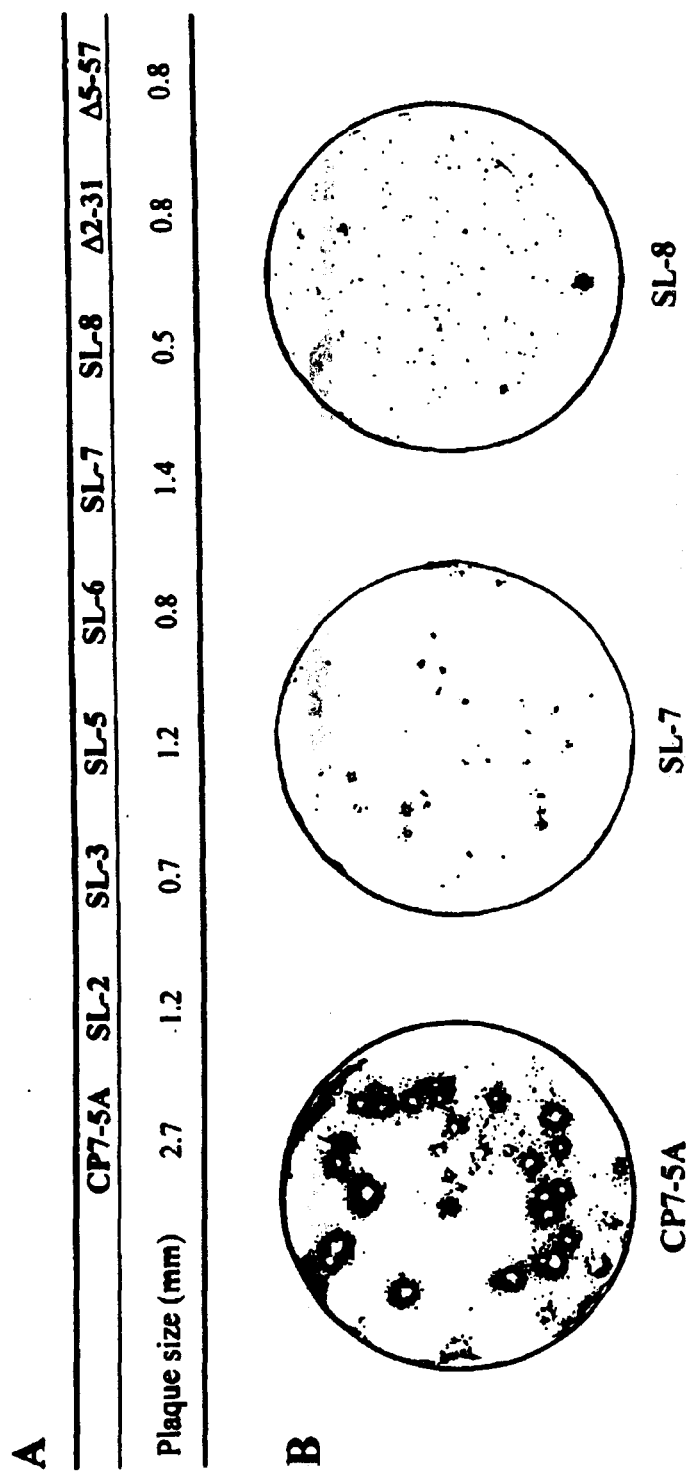
FIG. 7. Plaques produced by BVDV 5' NTR mutants at day 6 p.t. (A) Plaque size of CP7-5A, SL-2, SL-3, SL-5, SL-6, SL-7, SL-8, Δ2–31, and Δ5–57 in MDBK cells. The average plaque size of 20 randomly selected plaques is indicated. (B) As examples, the plaques generated by CP7-5A, SL-7, and SL-8 are shown.
Figure 8:
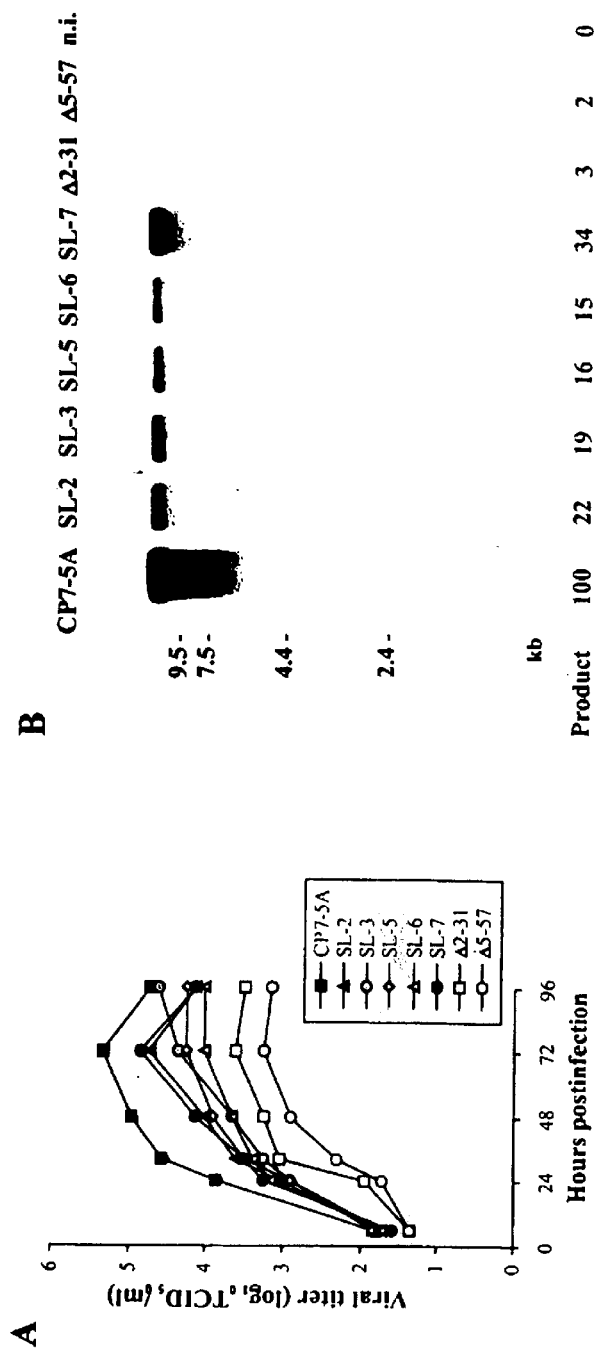
FIG. 8. (A) Growth curves of BVDV CP7-5A and mutant BVDV strains SL-2, SL-3, SL-5, SL-6, SL-7, Δ2–31, and Δ5–57 determined on MDBK cells infected at an MOI of 0.05. The titers of released virus were determined over a 4-day period. (B) Northern blot analysis of total RNA from MDBK cells infected with BVDV CP7-5A and the indicated mutant BVDV strains at an MOI of 0.05. The infected cells were processed in parallel to those used to determine the growth rates. RNAs were extracted at 48 h after infection. The blot was hybridized with a BVDV CP7-specific cDNA fragment. RNA ladder sizes in kilobases (kb) are indicated on the left. The intensity of bands was determined with a phosphorimager. The relative amounts of viral genomic RNAs are indicated below the blot.

<210> SEQ ID NO 1
<211> LENGTH: 48
<212> TYPE: DNA
<213> ORGANISM: Pestivirus sp.

<400> SEQUENCE: 1
tacgctagca tttaggtgac actatagtat acgaggttag gcaagttc        48

<210> SEQ ID NO 2
<211> LENGTH: 47
<212> TYPE: DNA
<213> ORGANISM: Pestivirus sp.

<400> SEQUENCE: 2
tacgctagca tttaggtgac actatagata cgaggttagg caagttc         47

<210> SEQ ID NO 3
<211> LENGTH: 46
<212> TYPE: DNA

-continued

<213> ORGANISM: Pestivirus sp.

<400> SEQUENCE: 3
tacgctagca tttaggtgac actatagtat aaggttaggc aagttc 46

<210> SEQ ID NO 4
<211> LENGTH: 61
<212> TYPE: DNA
<213> ORGANISM: Pestivirus sp.

<400> SEQUENCE: 4
tacgctagca tttaggtgac actatagtat acgaggttaa gttctcgtat acatattgga 60
c 61

<210> SEQ ID NO 5
<211> LENGTH: 51
<212> TYPE: DNA
<213> ORGANISM: Pestivirus sp.

<400> SEQUENCE: 5
tacgctagca tttaggtgac actataggcg acgaggttag gcaagttctc g 51

<210> SEQ ID NO 6
<211> LENGTH: 53
<212> TYPE: DNA
<213> ORGANISM: Pestivirus sp.

<400> SEQUENCE: 6
tacgctagca tttaggtgac actatagtat gtaaggttag gcaagttctc gta 53

<210> SEQ ID NO 7
<211> LENGTH: 60
<212> TYPE: DNA
<213> ORGANISM: Pestivirus sp.

<400> SEQUENCE: 7
tacgctagca tttaggtgac actatagtat acgagaactg gcaagttctc gtatacatat 60

<210> SEQ ID NO 8
<211> LENGTH: 82
<212> TYPE: DNA
<213> ORGANISM: Pestivirus sp.

<400> SEQUENCE: 8
tacgctagca tttaggtgac actatagtat acgaggttag gcaagttctc gtccccatat 60
tggacactct aaaaataatt ag 82

<210> SEQ ID NO 9
<211> LENGTH: 47
<212> TYPE: DNA
<213> ORGANISM: Pestivirus sp.

<400> SEQUENCE: 9
tacgctagca tttaggtgac actatagtat acatattgga cactcta 47

<210> SEQ ID NO 10
<211> LENGTH: 45
<212> TYPE: DNA
<213> ORGANISM: Pestivirus sp.

<400> SEQUENCE: 10
tacgctagca tttaggtgac actatagaca tattggacac tctaa 45

<210> SEQ ID NO 11
<211> LENGTH: 52
<212> TYPE: DNA
<213> ORGANISM: Pestivirus sp.

<400> SEQUENCE: 11
tacgctagca tttaggtgac actatagtat tggacactct aaaataatt ag        52

<210> SEQ ID NO 12
<211> LENGTH: 50
<212> TYPE: DNA
<213> ORGANISM: Pestivirus sp.

<400> SEQUENCE: 12
tacgctagca tttaggtgac actatagtat cctaggggac aaaaatcctc           50

<210> SEQ ID NO 13
<211> LENGTH: 46
<212> TYPE: DNA
<213> ORGANISM: Pestivirus sp.

<400> SEQUENCE: 13
tacgctagca tttaggtgac actatagtat cctccttagc gaaggc               46

<210> SEQ ID NO 14
<211> LENGTH: 96
<212> TYPE: RNA
<213> ORGANISM: Pestivirus sp.

<400> SEQUENCE: 14
guauacgaga uuagcuaaag uacucguaua cggauuggac gucgacaaac uuugaauugg    60
caacacaggg aaccuucccc ucggcgaagg ccgaaa                              96

<210> SEQ ID NO 15
<211> LENGTH: 88
<212> TYPE: RNA
<213> ORGANISM: Pestivirus sp.

<400> SEQUENCE: 15
guauacgagg uuagcucuuu ucgguauacg auauuggaua cacuaaauuu cgauugguc     60 uagggcaccc cuccagcgac ggccgaaa                                       88

<210> SEQ ID NO 16
<211> LENGTH: 89
<212> TYPE: RNA
<213> ORGANISM: Pestivirus sp.

<400> SEQUENCE: 16
guauacgagg uuaguucauu cucguguaca ugauuggaca aaucaaaauc ucaauuuggu    60
ucagggccuc ccuccagcga cggccgagc                                      89

<210> SEQ ID NO 17
<211> LENGTH: 100
<212> TYPE: RNA
<213> ORGANISM: Pestivirus sp.

<400> SEQUENCE: 17
guauacgagg uuaggcaagu ucucguauac auauuggaca cucuaaaaau aauuaggccu    60
aggggacaaa aauccuccuu agcgaaggcc gaaaagaggc                         100

-continued

<210> SEQ ID NO 18
<211> LENGTH: 98
<212> TYPE: RNA
<213> ORGANISM: Pestivirus sp.

<400> SEQUENCE: 18
guauacgagg uuaggcaagu ucucguauac auauuggaca cucuaaaaaa aaauaauuag 60
gccuagggga caaaaauccu ccuuagcgaa ggccgaaa 98

<210> SEQ ID NO 19
<211> LENGTH: 31
<212> TYPE: RNA
<213> ORGANISM: Pestivirus sp.

<400> SEQUENCE: 19
guauccuccu uagcgaaggc cgaaaagagg c 31

<210> SEQ ID NO 20
<211> LENGTH: 33
<212> TYPE: RNA
<213> ORGANISM: Pestivirus sp.

<400> SEQUENCE: 20
guauauccuc cuuagcgaag gccgaaaaga ggc 33

<210> SEQ ID NO 21
<211> LENGTH: 34
<212> TYPE: RNA
<213> ORGANISM: Pestivirus sp.

<400> SEQUENCE: 21
guauccuccu ccuuagcgaa ggccgaaaag aggc 34

<210> SEQ ID NO 22
<211> LENGTH: 96
<212> TYPE: RNA
<213> ORGANISM: Pestivirus sp.

<400> SEQUENCE: 22
guauacgaga auuagaaaag gcacucguau acguauuggg caauuaaaaa uaauaauuag 60
gccuagggaa caaaucccuc ucagcgaagg ccgaaa 96

<210> SEQ ID NO 23
<211> LENGTH: 93
<212> TYPE: RNA
<213> ORGANISM: Pestivirus sp.

<400> SEQUENCE: 23
guauacgaga auuugccuaa ccucguauac auauugggca uucuaaaaau aaauuaggcc 60
uaagggacaa auccuccuua gcgaaggccg aaa 93

<210> SEQ ID NO 24
<211> LENGTH: 87
<212> TYPE: RNA
<213> ORGANISM: Pestivirus sp.

<400> SEQUENCE: 24
guauacggga guagcucaug cccguauaca aaauuggaua uuccaaaacu cgauuggguu 60
agggagcccu ccuagcgacg gccgaac 87

What is claimed is:

1. An attenuated isolated pestivirus mutant having a growth-restricted phenotype relative to a wild-type pestivirus, said mutant comprising:

one or more mutations of stem loops 1a and/or 1b of the 5' nontranslated region (NTR) of the pestivirus genome, and wherein the mutated 5' end of the genome conserves the nucleotide sequence 5' -GUAU and expression of a viral poly protein from said genome is under the control of a homologous internal ribosome entry site (IRES).

2. The isolated pestivirus mutant of claim 1, wherein said growth-restricted phenotype is characterised by a small plaque size phenotype.

3. The isolated pestivirus mutant of claim 1, wherein the mutant comprises more than one mutation in the stem loops 1a and/or 1b.

4. The isolated pestivirus mutant of claim 1, wherein the one or more mutations is a deletion of one or more nucleotides.

5. The isolated pestivirus mutant of claim 4, wherein the one or more mutations is a deletion of stem loop 1a and a deletion in stem loop 1b.

6. The isolated pestivirus mutant of claim 4, wherein the mutation is a deletion of stem loops 1a and 1b, and wherein the nucleotide sequence after said deletion at the 5' end of the genome is GUAUAU or GUAUCCU.

7. The isolated pestivirus mutant of claim 4, wherein the loop portion of stem loop 1b contains five adenosine (A) residues.

8. The isolated pestivirus mutant of claim 1, wherein the one or more mutations is a deletion of stem loop 1a.

9. The isolated pestivirus mutant of claim 1, wherein the pestivirus is bovine viral diarrhea virus (BVDV).

10. The isolated pestivirus mutant of claim 9, wherein the pestivirus is BVDV-1 or BVDV-2.

11. A vaccine, comprising:

an immunogenically active isolated pestivirus mutant of claim 1 and a pharmaceutically acceptable carrier or diluent.

12. A vaccine of claim 11, wherein the vaccine provides a therapeutic effect in animals having pestivirus infections.

13. The vaccine of claim 11, wherein the vaccine further comprises adjuvant.

14. The vaccine of claim 11, wherein the vaccine is freeze-dried or frozen.

15. The vaccine according to claim 11, wherein the pestivirus mutant is BVDV and the vaccine further comprises an immunogen derived from one or more of bovine rotavirus, bovine respiratory syncytial virus, bovine herpesvirus type 1, bovine coronaviruses, parainfluenza type 3 virus, bovine paramyxovirus, foot and mouth disease virus, infectious bovine rhinotracheitis virus and *Pasteurella hemolytica*.

16. A vaccine, comprising:

an immunogenically effective dosage of the isolated pestivirus mutant of claim 1, and a pharmaceutically acceptable carrier and diluent.

17. The vaccine of claim 16, wherein the vaccine is prophylactic.

18. The vaccine of claim 16, wherein the vaccine further comprises an adjuvant.

19. The vaccine of claim 16, wherein the vaccine is freeze-dried or frozen.

20. The vaccine of claim 16, wherein the pestivirus mutant is BVDV and the vaccine further comprises an immunogen derived from one or more of bovine rotavirus, bovine respiratory syncytial virus, bovine herpesvirus type 1, bovine coronaviruses, parainfluenza type 3 virus, bovine paramyxovirus, foot and mouth disease virus, infectious bovine rhinotracheitis virus and *Pasteurella hemolytica*.

21. A method inducing immunity to a pestivirus infection, comprising:

administering to an animal the vaccine of claim 16.

22. A method of inducing immunity to a pestivirus infection, comprising:

administering to an animal the vaccine of claim 18.

23. A method of making a vaccine for the protection of an animal against a pestivirus infection, comprising:

mixing together the pestivirus mutant of claim 1 and a pharmaceutically acceptable carrier.

* * * * *